US011091469B2

(12) United States Patent
Candiani et al.

(10) Patent No.: US 11,091,469 B2
(45) **Date of Patent: *Aug. 17, 2021**

(54) CRYSTALLINE FORM OF N-[5-(3,5-DIFLUORO-BENZYL)-1H-INDAZOL-3-YL]-4-(4-METHYL-PIPERAZIN-1-YL)-2-(TETRAHYDRO-PYRAN-4-YLAMINO)-BENZAMIDE

(71) Applicant: NERVIANO MEDICAL SCIENCES S.R.L., Nerviano (IT)

(72) Inventors: Ilaria Candiani, Busto Arsizio (IT); Giovanni Ottaiano, Corbetta Milan (IT); Attilio Tomasi, Milan (IT)

(73) Assignee: NERVIANO MEDICAL SCIENCES S.R.L., Nerviano (IT)

( * ) Notice: Subject to any disclaimer, the term of this patent is extended or adjusted under 35 U.S.C. 154(b) by 0 days.

This patent is subject to a terminal disclaimer.

(21) Appl. No.: 16/912,965

(22) Filed: Jun. 26, 2020

(65) Prior Publication Data

US 2020/0325122 A1 Oct. 15, 2020

Related U.S. Application Data

(63) Continuation of application No. 16/301,826, filed as application No. PCT/EP2017/061919 on May 18, 2017, now Pat. No. 10,738,037.

(60) Provisional application No. 62/340,797, filed on May 24, 2016.

(51) Int. Cl.

| | |
|---|---|
| ***C07D 405/12*** | (2006.01) |
| ***C07D 405/14*** | (2006.01) |
| ***A61P 35/00*** | (2006.01) |

(52) U.S. Cl.

CPC ............ *C07D 405/14* (2013.01); *A61P 35/00* (2018.01); *C07D 405/12* (2013.01); *C07B 2200/13* (2013.01)

(58) Field of Classification Search

CPC ...... C07D 405/12; A61K 31/496; A61P 35/00
USPC ..................................... 544/371; 514/254.06
See application file for complete search history.

(56) References Cited

U.S. PATENT DOCUMENTS

| | | | |
|---|---|---|---|
| 10,738,037 B2 * | 8/2020 | Candiani ............. | C07D 405/14 |
| 2019/0169173 A1 | 6/2019 | Candiani et al. | |

FOREIGN PATENT DOCUMENTS

| | | |
|---|---|---|
| WO | 2009/013126 A1 | 1/2009 |
| WO | 2013/174876 A1 | 11/2013 |
| WO | 2015/124697 A1 | 8/2015 |

OTHER PUBLICATIONS

Acute Leukemia, Merck Manual (Online Edition) 6 pages, pp. 1-6 (2013).*

Majewska et al., Mammary analogoue secretory carcinoma of salivary glands: a new entity associated with ETV6 gene rearrangement, Virchows Arch (2015) 466: 245-254.*

Adriaenssens E. et al., "Nerve Growth Factor is a Potential Therapeutic Target in Breast Cancer", Cancer Research 68(2):346-351 (Jan. 15, 2008).

Bardelli A. et al., "Mutational Analysis of the Tyrosine Kinome in Colorectal Cancers", Science 300:949 (May 9, 2003).

Bergethon K. et al., "ROS1 Rearrangements Define a Unique Molecular Class of Lung Cancers", Journal of Clinical Oncology 30(8):863-870 (Mar. 10, 2012).

Brodeur G.M., "Neuroblastoma: Biological Insights into a Clinical Enigma", Nature Reviews Cancer 3:203-216 (Mar. 2003).

Brzezianska E. et al., "Rearrangements of NTRK1 Oncogene in Papilary Thyroid Carcinoma", Neuroendocrinology Letters 28(3):221-229 (2007).

Caira M.R., "Crystalline Polymorphism of Organic Compounds", Topics in Current Chemistry 198:163-208 (Jan. 1, 1998).

Cohen P., "Protein Kinases—the Major Drug Targets of the Twenty-First Century?", Nature Reviews Drug Discovery 309-315 (Apr. 2002).

Cohen P., "The Development and Therapeutic Potential of Protein Kinase Inhibitors", Current Opinion in Chemical Biology 3:459-465 (1999).

Dang C. et al., "Expression of Nerve Growth Factor Receptors is Correlated With Progression and Prognosis of Human Pancreatic Cancer", Journal of Gastroenterology and Hepatology 21:850-858 (2006).

Davidson B. et al., "Expression and Activation of the Nerve Growth Factor Receptor TrkA in Serous Ovarian Carcinoma", Clinical Cancer Research 9:2248-2259 (Jun. 2003).

Davies K.D. et al., "Resistance to ROS1 Inhibition Mediated by EGFR Pathway Activation in Non-Small Cell Lung Cancer", PLOS ONE 8(12):e82236 (Dec. 2013).

Davies K.D. et al., "Identifying and Targeting ROS1 Gene Fusions in Non-Small Cell Lung Cancer", Clinical Cancer Research 18(17):1-10 (2012).

Dionne C.A. et al., "Cell Cycle-Independent Death of Prostate Adenocarcinoma is Induced by the Trk Tyrosine Kinase Inhibitor CEP-751 (KT6587)", Clinical Cancer Research 4:1887-1898 (Aug. 1998).

Gura T., "Cancer Models: Systems for Identifying New Drugs Are Often Faulty", Science 278(5340):1041-1042 (Nov. 1997).

Hansen K. et al., "Autophagic Cell Death Induced by TrkA Receptor Activation in Human Glioblastoma Cells", Journal of Neurochemistry 103:259-275 (2007).

Hilfiker R. et al., "Relevance of Solid-State Properties for Pharmaceutical Products", Polymorphism: in the Pharmaceutical Industry 1-19 (Jan. 1, 2006).

Hu Y. et al., "Identification of Brain-Derived Neurotrophic Factor as a Novel Angiogenic Protein in Multiple Myeloma", Cancer Genetics and Cytogenetics 178:1-10 (2007).

Johnson J et al., "Relationships Between Drug Activity in NCI Preclinical In Vitro and In Vivo Models and Early Clinical Trials", British Journal of Cancer 84(10):1424-1431 (2001).

Krüttgen A. et al., "The Dark Side of the NGF Family: Neurotrophins in Neoplasias", Symposium: Brain Pathology 16:304-310 (2006).

Lee J. et al., "Identification of ROS1 Rearrangement in Gastric Adenocarcinoma", Cancer 119:1627-1635 (May 1, 2013).

(Continued)

*Primary Examiner* — Deepak R Rao

(74) *Attorney, Agent, or Firm* — Scully, Scott, Murphy & Presser, P.C.

(57) ABSTRACT

The present invention relates to a new crystalline form of N-[5-(3,5-difluoro-benzyl)-1H-indazol-3-yl]-4-(4-methyl-piperazin-1-yl)-2-(tetrahydro-pyran-4-ylamino)-benzamide, process for its preparation, its utility in treating diseases caused by deregulated protein kinase activity and pharmaceutical compositions containing it.

24 Claims, 2 Drawing Sheets

(56) References Cited

OTHER PUBLICATIONS

Marchetti A. et al., "Frequent Mutations in the Neurotrophic Tyrosine Receptor Kinase Gene Family in Large Cell Neuroendocrine Carcinoma of the Lung", Human Mutation 29(5):609-616 (2008).
Meyer J. et al., "Remarkable Leukemogenic Potency and Quality of a Constitutively Active Neurotrophin Receptor, TrkA", Leukemia 21:2171-2180 (2007).
Nakagawara A. et al., "Trk Receptor Tyrosine Kinases" A Bridge Between Cancer and Neural Development Cancer Letters 169:107-114 (2001).
Patapoutian A. et al., "Trk Receptors: Mediators of Neurotrophin Action", Current Opinion in Neurobiology 11:272-280 (2001).
Pearce H.L. et al., "Failure Modes in Anticancer Drug Discovery and Development", Cancer Drug Design and Discovery, Chapter 18, pp. 424-435 (2008).
Perez-Pinera P. et al., "The Trk Tyrosine Kinase Inhibitor K252a Regulates Growth of Lung Adenocarcinomas", Molecular and Cellular Biochemistry 295:19-26 (2007).
Pierotti M.A. et al., "Oncogenic Rearrangements of the NTRK1/NGF Receptor", Cancer Letters 232:90-98 (2006).
Shaw A.T. et al., "Crizotinib Versus Chemotherapy in Advanced ALK-Positive Lung Cancer", The New England Journal of Medicine 368(25):2385-2394 (Jun. 20, 2013).
Simone J.V., Introduction, Cecil Textbook of Medicine, 20th Edition, Oncology, vol. 1, pp. 1004-1010 (1996).
Stumpfova M. et al., "Zeroing in on ROS1 Rearrangements in Non-Small Cell Lung Cancer", Clinical Cancer Research 18(16):4222-4224 (Aug. 15, 2012).
Truzzi F. et al., "Neurotrophins and Their Receptors Stimulate Melanoma Cell Proliferation and Migration", Journal of Investigative Dermatology 128:2031-2040 (2008).
Velculescu V.E., "Defining the Blueprint of the Cancer Genome", Carcinogenesis 29(6):1087-1091 (2008).
Chemical Abstracts Registry No. 1108743-60-7 (2 pages) (2018).
International Search Report dated Jul. 4, 2017 received in International Application No. PCT/EP2017/061919.
U.S. Office Action dated Jun. 26, 2019 received in U.S. Appl. No. 16/301,826.
Ashizawa K., "Polymorphism of Drugs and Science of Crystallization", Maruzen Planet Co., Ltd., pp. 56-102 and 304-317 (2002).
Hirayama N., "Handbook for preparing crystals of organic compound", pp. 17-23, 37-40, 45-51, 57-65 (2008).
English-language translation of Japanese Notice of Rejection dated Mar. 31, 2020 received in Japanese Patent Application No. 2018-561474.

* cited by examiner

CRYSTALLINE FORM OF N-[5-(3,5-DIFLUORO-BENZYL)-1H-INDAZOL-3-YL]-4-(4-METHYL-PIPERAZIN-1-YL)-2-(TETRAHYDRO-PYRAN-4-YLAMINO)-BENZAMIDE

CROSS REFERENCE TO RELATED APPLICATIONS

This application is a continuation application of U.S. patent application Ser. No. 16/301,826, filed on Nov. 15, 2018, which is a national stage entry of PCT/EP2017/061919, filed on May 18, 2017, which claims the benefit of U.S. Provisional Application No. 62/340,797 filed on May 24, 2016, the entire contents of which are incorporated herein by reference.

FIELD OF THE INVENTION

The present invention relates to a new crystalline form of N-[5-(3,5-difluoro-benzyl)-1H-indazol-3-yl]-4-(4-methyl-piperazin-1-yl)-2-(tetrahydro-pyran-4-ylamino)-benzamide, process for its preparation, its utility in treating diseases caused by deregulated protein kinase activity and pharmaceutical compositions containing it.

BACKGROUND OF THE INVENTION

The malfunctioning of protein kinases (PKs) is the hallmark of numerous diseases. A large share of the oncogenes and proto-oncogenes involved in human cancers encode for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis, glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or deregulation see, for instance, Current Opinion in Chemical Biology 1999, 3, 459-465; Nature Rev. Drug Discov. 2002; and Carcinogenesis 2008, 29, 1087-1091.

A subset of PK is a group of membrane receptors with intrinsic protein-tyrosine kinase activity (RPTK). Upon binding of growth factors, RPTKs become activated and phosphorylate themselves and a series of substrates in the cytoplasm. Through this mechanism, they can transduce intracellular signallings for proliferation, differentiation or other biological changes. Structural abnormalities, over-expression and activation of RPTKs are frequently observed in human tumors, suggesting that constitutive ignition of the signal transduction leading to cell proliferation can result in malignant transformation. Anaplastic lymphoma kinase (ALK) is a tyrosine kinase receptor belonging to the insulin receptor subfamily of RPTKs: the ALK gene is located on chromosome 2 and is expressed mainly in neuronal cells, especially during development. The ALK gene is involved in a balanced chromosomal translocation with the Nucleophosmin (NPM) gene on chromosome 5 in a large subset of Anaplastic Large Cell Lymphomas (ALCL). In the ALK+ ALCL, as a result of the translocation, the NPM ubiquitous promoter drives an ectopic expression of the fusion protein in which the NPM moiety dimerizes and the ALK kinase domain undergoes auto-phosphorylation and becomes constitutively active.

Many data from the literature have demonstrated that the NPM-ALK fusion protein has a strong oncogenic potential and its ectopic expression is responsible for cellular transformation. Moreover, the constitutive expression of human NPM-ALK in mouse T-cell lymphocytes is sufficient for the development of lymphoid neoplasia in transgenic animals with a short period of latency.

ALCL is a defined disease characterized by the surface expression of the CD30 antigen (Ki-1), and accounts for 2% of adult and 13% of pediatric non-Hodgkin's lymphomas, affecting predominantly young male patients. ALK+ ALCL accounts for 70% of all ALCLs and is an aggressive disease with systemic signs, and frequent extranodal involvement (bone marrow, skin, bone, soft tissues).

About 15-20% of ALK-expressing ALCLs were found to bear a different chromosomal translocation, involving the cytoplasmic portion of ALK, with different N-terminal moieties, all resulting in constitutive activation of the ALK kinase domain.

Moreover, cell lines established from solid tumors of etodermal origin like melanomas, breast carcinomas, as well as neuroblastomas, glioblastomas, Ewings sarcomas, retinoblastomas, were found to express the ALK receptor.

ROS1 belongs to the insulin-receptor superfamily. Like other tyrosine kinase receptor molecules, it plays a role in relaying growth signals from the environment outside the cell into the cell's nucleus. It is 1 of 2 orphan receptor tyrosine kinase family members with no known binding ligand. Genetic changes in ROS1, such as gene rearrangements, mutations, or copy number increases, create oncogenes, which can lead to cancer (Stumpfova and Janne, 2012). ROS1 was discovered in NSCLC patients in the form of a fusion protein (6 different partners for ROS1) and is found in approximately 2% of patients with NSCLC (Bergethon et al., 2012; Davies et al, 2012). Two other ROS1 gene rearrangements have been detected in a variety of other canoers, including glioblastoma multiforme, cholangiocarcinoma, ovarian cancer, gastric adenocarcinoma, colorectal cancer, inflammatory myofibroblastic tumor, angiosarcoma, and epitheloid hemangioendothelioma (Lee et al., 2013; Davies and Doebele, 2013; Davies, et al., 2012; Shaw et al., 2013).

ROS1 gene rearrangements create fusion proteins with constitutively active kinase domains that activate downstream signaling pathways leading to onoogenic properties in cells, including uncontrolled proliferation and resistance to cell death with prolonged tumor cell survival. These pathways include Ras-ERK for cellular proliferation and the JAK-STAT and PI3K/AKT pathways, which regulate cell survival (anti-apoptosis) and proliferation. ROS1 fusion proteins may also activate the mTOR pathway, which is critical for the regulation of protein translation. Cancers that have these pathways activated tend to be more aggressive, with invasion and metastasis leading to poor survival of the patients (Davies and Doebele, 2013).

Trk's are the high affinity receptor tyrosine kinases activated by a group of soluble growth factors called neurotrophins (NT). The Trk receptor family has three members-TrkA, TrkB and TrkC. Among the neurotrophins are (i) nerve growth factor (NGF) which activates TrkA, (ii) brain-derived neurotrophic factor (BDNF) and NT-4/5 which activate TrkB and (iii) NT3 which activates TrkC. Trk's are widely expressed in neuronal tissue and are implicated in the maintenance, signaling and survival of neuronal cells (Patapoutian, A. et al., Current Opinion in Neurobiology, 2001, 11, 272-280). NTRK1 encodes the TrkA receptor tyrosine kinase. TrkA activates the PI3K/AKT, PKC and ERK1/2 pathways which promote cell growth and survival.

Recent literature has also shown that overexpression, activation, amplification and/or mutation of Trk's are associated with many cancers including neuroblastoma (Brodeur, G. M., Nat. Rev. Cancer 2003, 3, 203-216), ovarian cancer (Davidson. B., et al., Clin. Cancer Res. 2003, 9, 2248-2259), breast cancer (Kruettgen et al, Brain Pathology 2006, 16: 304-310), prostate cancer (Dionne et al, Clin. Cancer Res. 1998, 4(8): 1887-1898), pancreatic cancer (Dang et al, Journal of Gastroenterology and Hepatology 2006, 21(5): 850-858), multiple myeloma (Hu et al, Cancer Genetics and Cytogenetics 2007, 178: 1-10), astrocytoma and medulloblastoma (Kruettgen et al, Brain Pathology 2006, 16: 304-310) glioma (Hansen et al, Journal of Neurochemistry 2007, 103: 259-275), melanoma (Truzzi et al, Journal of Investigative Dermatology 2008, 128(8): 2031-2040, thyroid carcinoma (Brzezianska et al, Neuroendocrinology Letters 2007, 28(3), 221-229), lung adenocarcinoma (Perez-Pinera et al, Molecular and Cellular Biochemistry 2007, 295(1&2), 19-26), large cell neuroendocrine tumors (Marchetti et al, Human Mutation 2008, 29(5), 609-616), and colorectal cancer (Bardelli, A., Science 2003, 300, 949). In preclinical models of cancer, Trk inhibitors are efficacious in both inhibiting tumor growth and stopping tumor metastasis. In particular, non-selective small molecule inhibitors of Trk A, B and C and Trk/Fc chimeras were efficacious in both inhibiting tumor growth and stopping tumor metastasis (Nakagawara, A. (2001) Cancer Letters 169:107-114; Meyer, J. et al. (2007) Leukemia, 1-10; Pierotti, M. A and Greco A., (2006) Cancer Letters 232:90-98; Eric Adriaenssens, E. et al. Cancer Res (2008) 68:(2) 346-351) (Truzzi et al, Journal of Investigative Dermatology 2008, 128(8): 2031-2040. Therefore, an inhibitor of the Trk family of kinases is expected to have utility in the treatment of cancer.

In conclusion, interfering with ALK or ROS1 signaling likely represents a specific and effective way to block tumor cell proliferation in ALCL and possibly other indications. The insulin-like growth factor 1 receptor (IGF-1R, IGF1R) is also a member of the insulin receptor subfamily of RTKs. In addition, interfering with TrkA, TrkB and/or TrkC signaling, or a combination thereof, represents a specific and effective way to block tumor cell proliferation in various cancers, including, but not limited to, non-small cell lung cancer, papillary thyroid cancer, neuroblastoma, pancreatic cancer and colorectal cancer.

SUMMARY OF THE INVENTION

The international patent application WO2009/013126 (in the name of Nerviano Medical Sciences SrI) describes and claims the free-base form of N-[5-(3,5-Difluoro-benzyl)-1H-indazol-3-yl]-4-(4-methyl-piperazin-1-yl-2-(tetrahydro-pyran-4-ylamino)-benzamide, which has the following formula (I)

(I)

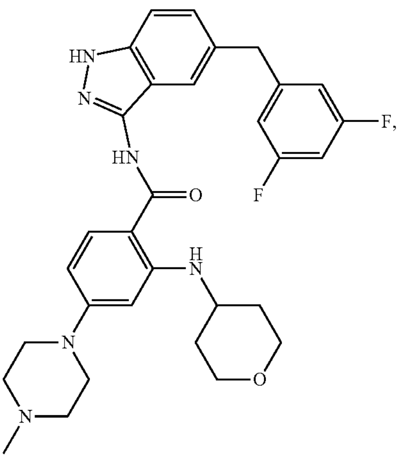

has been assigned Chemical Abstracts Registry No. 1108743-60-7 and has been assigned the international non-proprietary name (INN) entrectinib.

The compound of formula (i) is active as a kinase inhibitor, more particularly an inhibitor of ALK, ROS1, TrkA, TrkB, and Trk C kinases, and it is thus useful in the treatment of a variety of cancers and cell proliferative disorders as disclosed in international patent application WO2015124697 (in the name of Ignyta Inc. and Nerviano Medical Sciences SrI) and as demonstrated by clinical trials in human patients having cancer. Entrectinib has been tested clinically in cancer patients with various types of cancerous, solid tumors, the cells of which contain one or more genetic alterations in at least one target gene in the cancer patient, wherein the at least one target gene is selected from ALK, ROS1, SORT1, NTRK1, NTRK2, and NTRK3. Aug. 15, 2015, the findings of such clinical trials showed that a total of 92 patients with a range of solid tumors had been dosed across both clinical trials, with 9 patients treated at or above the recommended Phase II dose beyond six months and 1 patient beyond one year. Across the Phase I studies, the most frequent (>10% incidence) treatment-related adverse events were fatigue, dysgeusia, paresthesia, nausea, and myalgia. Seven of these were Grade 3 in severity, consisting of fatigue (4 patients), cognitive impairment (2 patients), and diarrhea (1 patient). No Grade 4 or Grade 5 treatment-related adverse events were observed. Across the Phase I studies, there were three treatment-related serious adverse events: Grade 3 cognitive impairment and Grade 3 myocarditis, both of which occurred at doses above the recommended Phase II dose, and Grade 2 fatigue. All events were reversible and resolved upon dose modification. Pharmacokinetic measurements showed dose-proportional increases across the daily dosing regimens evaluated, with a half-life compatible with once-daily dosing. The recommended Phase II dose was determined to be 600 mg, taken orally once per day. A total of 18 patients across the Phase I studies met our expected Phase 2 eligibility criteria, which include the presence of NTRK1, NTRK2, NTRK3, ROS1 or ALK genetic alterations which are fusions, as opposed to other types of molecular alterations; the patient not having been previously treated with an ALK inhibitor or a ROS1 inhibitor and treatment at or above the recommended Phase II dose. In the Phase I clinical trials, the response rate, defined as complete and partial responses by Response Evaluation Criteria In Solid Tumors, or RECIST criteria, in the 18 patients who met the expected Phase 2 eligibility criteria across both studies was 72%, based on 13 responses out of 18 treated patients, as assessed by the clinical sites. Nine of these responders remained on study treatment with durable responses of up to 21 treatment cycles. An additional 3 patients remained on study with stable disease. The responses included (a) 3 responses out of 4 patients with NTRK1, NTRK2 or NTRK3 gene rearrangements, including patients with non-small cell lung cancer, or NSCLC, colorectal cancer and salivary gland cancer, with one of the responding patients remaining on treatment at 6 months; a fourth patient with an astrocytoma remains on treatment after two months with stable disease, (b) 6 responses, including one complete response, out of 8 patients with ROS1 gene rearrangements, all of which were in NSCLC. All of the patients who responded remain on treatment, the longest at 21 months, and (c) 4 responses out of 6 patients with ALK gene rearrangements, including two NSCLC patients and two patients with other solid tumors; 2 of the 4 responders subsequently progressed.

Two preparations of this compound are described respectively in example 2 (step i') and example 7 of the above cited application WO2009/013126. The process described in example 2 comprises, essentially, adding 5-(3,5-difluoro-benzyl)-1H-indazol-3-ylamine to 4-(4-methyl-piperazin-1-yl)-2-[(tetrahydro-pyran-4-yl)-(2,2,2-trifluoro-acetyl)-amino]-benzoic acyl chloride and then deprotecting with an organic base at high temperature to give the desired amide of formula (I), after purification by column chromatography and crystallization.

The other process described in example 7 of the above cited patent application is a conversion which comprises, essentially, reacting 2-amino-N-[5-(3,5-difluoro-benzyl)-1H-indazol-3-yl]-4-(4-methyl-piperazin-1-yl)-benzamide with tetrahydro-pyran-4-one in presence of trifluoroacetic acid and tetramethylammonium triacetoxyborohydride to give the desired amide of formula (I), after purification by column chromatography.

However, the solid form of these preparations was not disclosed in the WO20091013126 application. The products obtained by following the experimental procedures in example 2 (step i') and example 7 described in application WO2009/013126 were disclosed in application WO2013/174876 (in the name of Nerviano Medical Sciences Srl). In particular, example the procedure disclosed in example 2 (step i') was found to yield a crystalline solvate of the compound of formula (I) containing ethyl acetate and n-hexane (hereinafter referred to as "Form 3"). Following the experimental procedures in example 7 of the WO2009/013126 application was found to yield an amorphous form of the compound of formula (I).

Two novel solid forms of the compound of formula (I) have been disclosed in application WO2013/174876, together with a process for their preparation, which provides the product in an industrially advantageous and highly reproducible manner with high purity and characteristics suitable for administration to humans and at a reduced cost. This new process was characterized by reaction of an acyl chloride with an indazol-3-ylamine followed by deprotection under mild basic conditions and treatment of the final amorphous compound with a mixture of ethanol and water in presence of seeds, to give the desired compound of formula (I) in crystalline a form designated "form 1" or with a mixture of ethanol and water, to give the desired compound of formula (I) in a crystalline form designated "form 2." The crystalline, solvate form of the compound of formula (I), which is a solvate of ethyl acetate and hexane found to have resulted from following the experimental procedure in application WO2009/013126 was also disclosed in application WO2013/174876 and was designated as "form 3" therein.

However there is still a need in therapy to understand the polymorphic behaviour of the potential pharmaceutical compound defined above and to standardize the methods for obtaining its different solid forms. In fact, the identification and characterization of the polymorphic forms together with the definitions of the experimental conditions for obtaining them is very important for a compound endowed with pharmacological activity like the compound of formula (I) defined above, because the polymorphism of a compound that could be used as active ingredient in a pharmaceutical composition can influence many aspects of the final drug, such as the pharmacokinetic and bioavailability, its toxicological profile, solubility and other phisico-chemical properties of the bulk powder.

In this respect, it has been now unexpectedly and surprisingly found that the above compound of formula (I) may also exist in a crystalline, unsolvated form not previously disclosed. This novel crystalline form of compound (I) may be referred to herein, unless otherwise specified, as "crystalline Form 4" or "Form 4" of the compound of formula (I).

It has been surprisingly found that Form 4 of the compound of formula (I) is exhibits greater thermodynamic stability at temperature of about 40° C. or higher vis-à-vis the three known crystalline forms disclosed in WO20131174876, one of which is a solvate with ethyl acetate and hexane. Form 4 of the compound of formula (I) may also offer advantages in the preparation of dosage forms or medicaments useful for the treatment of cancer patients with various types of cancerous, solid tumors, the cells of which contain one or more genetic alterations in at least one target gene, wherein the at least one target gene is selected from ALK, ROS1, SORT1, NTRK1, NTRK2, and NTRK3. Form 4 of the compound of formula (I) may also offer advantages in the methods of treatment of patients having cancer, comprising administering to the patient a therapeutically effective amount of Form 4 of the compound of formula (I) to the patient.

Preparation of dosage forms or medicaments useful for the treatment of cancer patients with various types of cancerous, solid tumors, the cells of which contain one or more genetic alterations in at least one target gene, wherein the at least one target gene is selected from ALK, ROS1, SORT1, NTRK1, NTRK2, and NTRK3.

The new crystalline Form 4 has been characterized through the x-ray powder diffraction (XRPD) and differential scanning calorimetry (DSC) techniques.

DESCRIPTION OF THE DRAWINGS

The invention is also illustrated by reference to the accompanying drawings described below.

DETAILED DESCRIPTION

Figure 1:
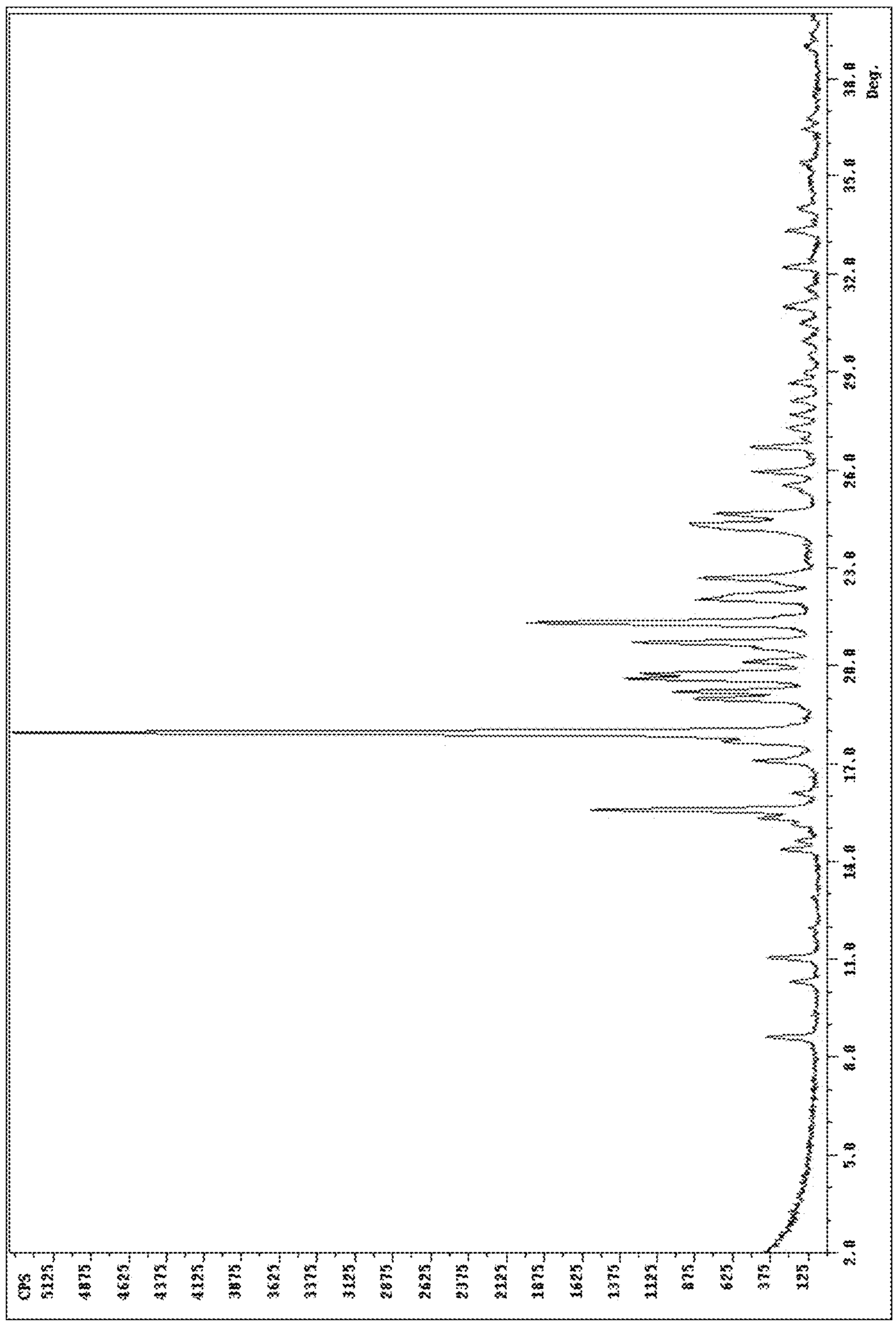
FIG. 1 shows the x-ray powder diffraction pattern (XRPD) of the crystalline Form 4; 2-Theta angles (deg) are reported on the x axis while intensity (CPS) is reported on the y axis.

As used herein, the term "N-[5-(3,5-Difluoro-benzyl)-1H-indazol-3-yl]-4-(4-methyl-piperazin-1-yl)-2-(tetrahydro-pyran-4-ylamino)-benzamide" means the compound having the chemical structure:

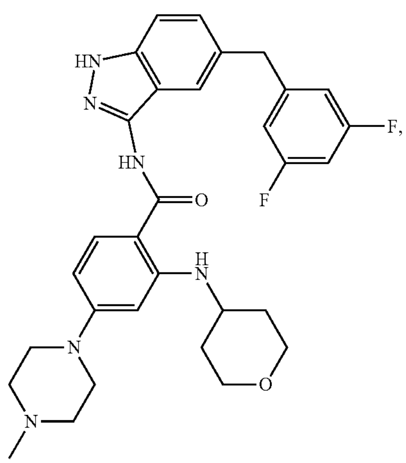

Which has been assigned Chemical Abstracts Registry No. 1108743-60-7 and has been assigned the international non-proprietary name (INN) entrectinib.

The use of the term "about" includes and describes the value or parameter per se. For instance, "about x" includes and describes "x" per se. In some embodiments, the term "about" when used in association with a measurement, or used to define a value, a unit, a constant, or a range of values, refers to a variation ±10%, unless indicated otherwise. For example, "about 40° C." in some embodiments includes 36° C. to 44° C.

The use of the term "adding" herein does not limit the order, method or how the materials being added are combined. For instance, "adding A to B" may also describe "adding B to A".

As used herein, the terms "administration" and "administering" mean the delivery of a bioactive composition or formulation to a subject by an administration route including, but not limited to, oral, intravenous, intra-arterial, intramuscular, intraperitoneal, subcutaneous, intramuscular, topically, or combinations thereof. In some embodiments, the administration to a subject is oral.

As used herein, the term "ALK" means anaplastic lymphoma kinase receptor or CD246 (cluster of differentiation 246), which is an enzyme that in humans is encoded by the ALK gene and also has the UniProt identified ALK_HUMAN.

As used herein, the terms "cancer" or "tumor" may be used interchangeably. These terms mean the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell, such as a leukemia cell. These terms include a solid tumor, a soft tissue tumor, or a metastatic lesion. As used herein, the term "cancer" includes premalignant, as well as malignant cancers. In certain embodiments, the cancer is a solid tumor, a soft tissue tumor, or a metastatic lesion. The terms also refer to solid tumors named for the type of cells that form them, cancer of blood, bone marrow, or the lymphatic system. Examples of solid tumors include, but are not limited to, sarcomas and carcinomas. Examples of cancers of the blood include, but are not limited to, leukemias, lymphomas and myeloma. The terms include, but are not limited to, a primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of different type from latter one. As used herein "cancer" refers to any malignant and/or invasive growth or tumor caused by abnormal cell growth.

As used herein, the term "crystalline" means a solid phase in which a material has a regular ordered internal structure at the molecular level and gives a distinctive x-ray diffraction pattern with defined peaks.

The term "other therapeutic agents" as used herein means, but is not limited to, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

The terms "patient" and/or "subject" as used herein mean animal, such as mammal (including human), that has been or will be the object of treatment, observation or experiment. In some embodiments, the subject or patient is a human.

The term "pharmaceutical acceptable excipient" means diluents, disintegrants, precipitation inhibitors, surfactants, glidants, lubricants and other excipients and vehicles with which a compound is administered to a subject or patient.

As used herein, "ROS1" means the ROS1 receptor tyrosine-protein kinase having the UniProt designation ROS1_HUMAN and encoded by the ROS1 gene.

The term "therapeutically effective amount" as used herein means the amount of a compound or pharmaceutical composition sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of ALK, TrkA, TrkB, TrkC, and ROS1 activity or a combination thereof.

The term "tropomyosin receptor kinase," as used herein, means the family of tropomyosin receptor kinases (Trks) that are activated by peptide hormones of the neurotrophin family and include, but are not limited to, TrkA, TrkB, and TrkC. As used herein, the term "TrkA" means wild-type tropomyosin receptor kinase A having the UniProt identifier NTRK1_HUMAN and encoded by the NTRK1 gene. As used herein, the term "TrkB" means wild-type tropomyosin receptor kinase B having the UniProt identifier NTRK2_HUMAN and encoded by the NTRK2 gene. As used herein, the term "TrkC" means wild-type tropomyosin receptor kinase C having the UniProt identifier NTRK3_HUMAN and encoded by the NTRK3 gene. TrkA, TrkB and TrkC are also referred to by those having ordinary skill in the art as Trk1, Trk2 and Trk3, respectively. A reference to TrkA is a reference to Trk1. A reference to TrkB is a reference to Trk2. A reference to TrkC is a reference to Trk3.

In one embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising a peak at a 2-theta value of about 8.6 degrees. In another embodiment is provided such a crystalline form, wherein said crystalline form is unsolvated.

In another embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising a peak at a 2-theta value of about 8.6±0.5 degrees. In another embodiment is provided such a crystalline form, wherein said crystalline form is unsolvated.

In another embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising a peak at a 2-theta value of about 8.6±0.2 degrees. In another embodiment is provided such a crystalline form, wherein said crystalline form is unsolvated.

In one embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising a peak at a 2-theta value of about 15.6 degrees. In another embodiment is provided such a crystalline form, wherein said crystalline form is unsolvated.

In another embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising a peak at a 2-theta value of about 15.6±0.5 degrees. In another embodiment is provided such a crystalline form, wherein said crystalline form is unsolvated.

In another embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising a peak at a 2-theta value of about 15.6±0.2 degrees. In another embodiment is provided such a crystalline form, wherein said crystalline form is unsolvated.

In one embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising a peak at a 2-theta value of about 17.9 degrees. In another embodiment is provided such a crystalline form, wherein said crystalline form is unsolvated.

In another embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising a peak at a 2-theta value of about 17.9±0.5 degrees. In another embodiment is provided such a crystalline form, wherein said crystalline form is unsolvated.

In another embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising a peak at a 2-theta value of about 17.9±0.2 degrees. In another embodiment is provided such a crystalline form, wherein said crystalline form is unsolvated.

In another embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising peaks at a 2-theta value of about 15.6 and 17.9 degrees. In another embodiment is provided such a crystalline form, wherein said crystalline form is unsolvated.

In another embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising peaks at a 2-theta value of about 15.6 and 17.9±0.5 degrees. In another embodiment is provided such a crystalline form, wherein said crystalline form is unsolvated.

In another embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising peaks at a 2-theta value of about 15.6 and 17.9±0.2 degrees. In another embodiment is provided such a crystalline form, wherein said crystalline form is unsolvated.

In another embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising peaks at a 2-theta value of about 15.6, 17.9 and 39.0 degrees. In another embodiment is provided such a crystalline form, wherein said crystalline form is unsolvated.

In another embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising peaks at a 2-theta value of about 15.6, 17.9 and 39.0±0.5 degrees. In another embodiment is provided such a crystalline form, wherein said crystalline form is unsolvated.

In another embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising peaks at a 2-theta value of about 15.6, 17.9 and 39.0±0.2 degrees. In another embodiment is provided such a crystalline form, wherein said crystalline form is unsolvated.

In another embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising peaks at a 2-theta value of about 8.6, 10.3, 11.0, 11.9, 14.3, 14.6, 15.1, 15.3, 15.6, 16.1, 17.1, 17.9, 19.0, 19.2, 19.6, 19.7, 20.1, 20.7, 21.3, 22.1, 22.7, 24.3, 24.6, 25.3, 25.5, 25.9, 26.7, 26.9, 27.3, 27.7, 28.1, 28.6, 29.0, 29.5, 29.9, 30.5, 31.0, 31.6, 32.2, 33.3, 34.0, 35.4, 36.4, 36.8 and 39.0 degrees. In another embodiment is provided such a crystalline form, wherein said crystalline form is unsolvated.

In another embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising peaks at a 2-theta value of about 8.6, 10.3, 11.0, 11.9, 14.3, 14.6, 15.1, 15.3, 15.6, 16.1, 17.1, 17.9, 19.0, 19.2, 19.6, 19.7, 20.1, 20.7, 21.3, 22.1, 22.7, 24.3, 24.6, 25.3, 25.5, 25.9, 26.7, 26.9, 27.3, 27.7, 28.1, 28.6, 29.0, 29.5, 29.9, 30.5, 31.0, 31.6, 32.2, 33.3, 34.0, 35.4, 36.4, 36.8 and 39.0±0.5 degrees. In another embodiment is provided such a crystalline form, wherein said crystalline form is unsolvated.

In another embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising peaks at a 2-theta value of about 8.6, 10.3, 11.0, 11.9, 14.3, 14.6, 15.1, 15.3, 15.6, 16.1, 17.1, 17.9, 19.0, 19.2, 19.6, 19.7, 20.1, 20.7, 21.3, 22.1, 22.7, 24.3, 24.6, 25.3, 25.5, 25.9, 26.7, 26.9, 27.3, 27.7, 28.1, 28.6, 29.0, 29.5, 29.9, 30.5, 31.0, 31.6, 32.2, 33.3, 34.0, 35.4, 36.4, 36.8 and 39.0 degrees±0.2 degrees. In another embodiment is provided such a crystalline form, wherein said crystalline form is unsolvated.

In another embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by exhibiting a peak in a differential scanning calorimetry scan of from about 200° C. to about 205° C.

In another embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by exhibiting a peak in a differential scanning calorimetry scan of from about 200° C. to about 205° C., and an x-ray powder diffraction pattern comprising a peak at a 2-theta value of about 15.6 degrees. In another embodiment is provided such a crystalline form, wherein said crystalline form is unsolvated.

In another embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by exhibiting a peak in a differential scanning calorimetry scan of from about 200° C. to about 205° C., and an x-ray powder diffraction pattern comprising a peak at a 2-theta value of about 15.6±0.5 degrees. In another embodiment is provided such a crystalline form, wherein said crystalline form is unsolvated.

In another embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by exhibiting a peak in a differential scanning calorimetry scan of from about 200° C. to about 205° C., and an x-ray powder diffraction pattern comprising a peak at a 2-theta value of about 15.6±0.2 degrees. In another embodiment is provided such a crystalline form, wherein said crystalline form is unsolvated.

In another embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by exhibiting a peak in a differential scanning calorimetry scan of from about 200° C. to about 205° C., and an x-ray powder diffraction pattern comprising a peak at a 2-theta value of about 15.6 and 17.9 degrees. In another embodiment is provided such a crystalline form, wherein said crystalline form is unsolvated.

In another embodiment is provided a crystalline form of N-[5-(3,5-difluoro-benzyl)-1H-indazol-3-yl]-4-(4-methy-piperazin-1-yl)-2-(tetrahydro-pyran-4-ylamino)-benzamide, wherein said crystalline form is characterized by exhibiting a peak in a differential scanning calorimetry scan of from about 200° C. to about 205° C., and an x-ray powder diffraction pattern comprising a peak at a 2-theta value of about 15.6 and 17.9±0.5 degrees. In another embodiment is provided such a crystalline form, wherein said crystalline form is unsolvated.

In another embodiment is provided a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by exhibiting a peak in a differential scanning calorimetry scan of from about 200° C. to about 205° C., and an x-ray powder diffraction pattern comprising a peak at a 2-theta value of about 15.6 and 17.9±0.2 degrees. In another embodiment is provided such a crystalline form, wherein said crystalline form is unsolvated.

In another embodiment is provided a pharmaceutical composition comprising a therapeutically effective amount of a crystalline form of N-[5-(3,5-Difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising a peak at a 2-theta value of about 15.6 degrees, and one or more pharmaceutically acceptable excipients.

In another embodiment is provided a pharmaceutical composition comprising a therapeutically effective amount of a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising a peak at a 2-theta value of about 15.6±0.5 degrees, and one or more pharmaceutically acceptable excipients.

In another embodiment is provided a pharmaceutical composition comprising a therapeutically effective amount of a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising a peak at a 2-theta value of about 15.6±0.2 degrees, and one or more pharmaceutically acceptable excipients.

In another embodiment is provided a pharmaceutical composition comprising a therapeutically effective amount of a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising peaks at a 2-theta value of about 15.6 and 17.9 degrees.

In another embodiment is provided a pharmaceutical composition comprising a therapeutically effective amount of a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising peaks at a 2-theta value of about 15.6 and 17.9±0.5 degrees.

In another embodiment is provided a pharmaceutical composition comprising a therapeutically effective amount of a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising peaks at a 2-theta value of about 15.6 and 17.9±0.2 degrees.

In another embodiment is provided a pharmaceutical composition comprising a therapeutically effective amount of a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by exhibiting a peak in a differential scanning calorimetry scan of from about 200° C. to about 205° C.

In another embodiment is provided a pharmaceutical composition comprising a therapeutically effective amount of a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by exhibiting a peak in a differential scanning calorimetry scan of from about 200° C. to about 205° C., and an x-ray powder diffraction pattern comprising a peak at a 2-theta value of about 15.6 degrees.

In another embodiment is provided a pharmaceutical composition comprising a therapeutically effective amount of a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by exhibiting a peak in a differential scanning calorimetry scan of from about 200° C. to about 205° C., and an x-ray powder diffraction pattern comprising a peak at a 2-theta value of about 15.6±0.5 degrees.

In another embodiment is provided a pharmaceutical composition comprising a therapeutically effective amount of a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by exhibiting a peak in a differential scanning calorimetry scan of from about 200° C. to about 205° C., and an x-ray powder diffraction pattern comprising a peak at a 2-theta value of about 15.6±0.2 degrees.

In another embodiment is provided a pharmaceutical composition comprising a therapeutically effective amount of a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by exhibiting a peak in a differential scanning calorimetry scan of from about 200° C. to about 205° C., and an x-ray powder diffraction pattern comprising a peak at a 2-theta value of about 15.6 and 17.9 degrees. In another embodiment is provided such a crystalline form, wherein said crystalline form is unsolvated.

In another embodiment is provided a pharmaceutical composition comprising a therapeutically effective amount of a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by exhibiting a peak in a differential scanning calorimetry scan of from about 200° C. to about 205° C., and an x-ray powder diffraction pattern comprising a peak at a 2-theta value of about 15.6 and 17.9±0.5 degrees.

In another embodiment is provided a pharmaceutical composition comprising a therapeutically effective amount of a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by exhibiting a peak in a differential scanning calorimetry scan of from about 200° C. to about 205° C., and an x-ray powder diffraction pattern comprising a peak at a 2-theta value of about 15.6 and 17.9±0.2 degrees.

In another embodiment is provided method of treating a patient having cancer, comprising administering to said patient a therapeutically effective amount of a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising a peak at a 2-theta value of about 15.6 degrees.

In another embodiment is provided method of treating a patient having cancer, comprising administering to said patient a therapeutically effective amount of a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising a peak at a 2-theta value of about 15.6±0.5 degrees.

In another embodiment is provided method of treating a patient having cancer, comprising administering to said patient a therapeutically effective amount of a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising a peak at a 2-theta value of about 15.6±0.2 degrees.

In another embodiment is provided method of treating a patient having cancer, comprising administering to said patient a therapeutically effective amount of a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising peaks at a 2-theta value of about 15.6 and 17.9 degrees.

In another embodiment is provided method of treating a patient having cancer, comprising administering to said patient a therapeutically effective amount of a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising peaks at a 2-theta value of about 15.6 and 17.9±0.5 degrees.

In another embodiment is provided method of treating a patient having cancer, comprising administering to said patient a therapeutically effective amount of a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising peaks at a 2-theta value of about 15.6 and 17.9±0.2 degrees.

In another embodiment is provided method of treating a patient having cancer, comprising administering to said patient a pharmaceutical composition comprising a therapeutically effective amount of a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising a peak at a 2-theta value of about 15.6 degrees, and one or more pharmaceutically acceptable excipients.

In another embodiment is provided method of treating a patient having cancer, comprising administering to said patient a pharmaceutical composition comprising a therapeutically effective amount of a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising a peak at a 2-theta value of about 15.6±0.5 degrees, and one or more pharmaceutically acceptable excipients.

In another embodiment is provided method of treating a patient having cancer, comprising administering to said patient a pharmaceutical composition comprising a therapeutically effective amount of a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising a peak at a 2-theta value of about 15.6±0.2 degrees, and one or more pharmaceutically acceptable excipients.

In another embodiment is provided method of treating a patient having cancer, comprising administering to said patient a pharmaceutical composition comprising a therapeutically effective amount of a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising peaks at a 2-theta value of about 15.6 and 17.9 degrees.

In another embodiment is provided method of treating a patient having cancer, comprising administering to said patient a pharmaceutical composition comprising a therapeutically effective amount of a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising peaks at a 2-theta value of about 15.6 and 17.9±0.5 degrees.

In another embodiment is provided method of treating a patient having cancer, comprising administering to said patient a therapeutically effective amount of pharmaceutical composition comprising a crystalline form of N-[5-(3,5-difluoro-benzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising peaks at a 2-theta value of about 15.6 and 17.9±0.2 degrees.

In other embodiments are provided any of the methods of treating a patient having cancer described herein wherein said cancer is selected from breast cancer, lung cancer, colorectal cancer, prostate cancer, ovarian cancer, endometrial cancer, gastric cancer, clear cell renal cell carcinoma, invasive ductal carcinoma (breast), uveal melanoma, multiple myeloma, rhabdomyosarcoma, Ewing's sarcoma, Kaposi's sarcoma, pancreatic cancer, medulloblastoma, anaplastic large cell lymphomas (ALCL), neuroblastoma, rhabdomyosarcoma, glioblastoma, inflammatory myofibroblastic tumor, melanoma, retinoblastoma, non-small cell lung cancer (NSCLC), salivary gland cancer, and mammary analog secretory carcinoma (MASC).

In other embodiments are provided any of the methods of treating a patient having cancer described herein wherein said cancer is selected from breast cancer, lung cancer, colorectal cancer, prostate cancer, gastric cancer, medulloblastoma, neuroblastoma, glioblastoma, melanoma, non-small cell lung cancer (NSCLC), salivary gland cancer, and mammary analog secretory carcinoma (MASC).

In other embodiments are provided any of the methods of treating a patient having cancer described herein wherein said cancer is selected from breast cancer, lung cancer, colorectal cancer, medulloblastoma, neuroblastoma, glioblastoma, melanoma, non-small cell lung cancer (NSCLC), salivary gland cancer, and mammary analog secretory carcinoma (MASC).

In other embodiments are provided any of the methods of treating a patient having cancer described herein wherein said cancer is selected from colorectal cancer, neuroblastoma, glioblastoma, melanoma, non-small cell lung cancer (NSCLC), salivary gland cancer, and mammary analog secretory carcinoma (MASC).

In other embodiments are provided any of the methods of treating a patient having cancer described herein wherein said cancer is colorectal cancer.

In other embodiments are provided any of the methods of treating a patient having cancer described herein wherein said cancer is neuroblastoma.

In other embodiments are provided any of the methods of treating a patient having cancer described herein wherein said cancer is glioblastoma.

In other embodiments are provided any of the methods of treating a patient having cancer described herein wherein said cancer is melanoma.

In other embodiments are provided any of the methods of treating a patient having cancer described herein wherein said cancer is non-small cell lung cancer (NSCLC).

In other embodiments are provided any of the methods of treating a patient having cancer described herein wherein said cancer is salivary gland cancer.

In other embodiments are provided any of the methods of treating a patient having cancer described herein wherein said cancer is mammary analog secretory carcinoma (MASC).

In other embodiments are provided any of the methods of treating a patient having cancer described herein, wherein said cancer is locally advanced or metastatic.

The present invention also discloses a method of preparation of the crystalline Form 4 defined above comprising the following steps:

a) adding the acyl chloride of formula (II):

(II)

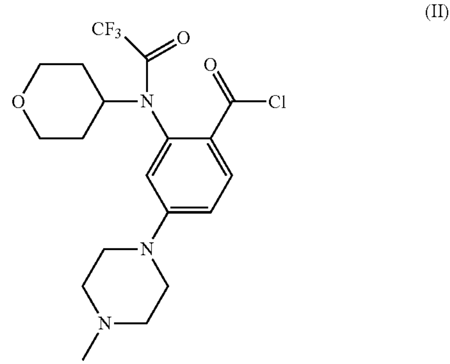 [SMILES: CN1CCN(c2ccc(C(=O)Cl)c(N(C(=O)C(F)(F)F)C3CCOCC3)c2)CC1]

to the indazol-3-ylamine of formula (III):

(III)

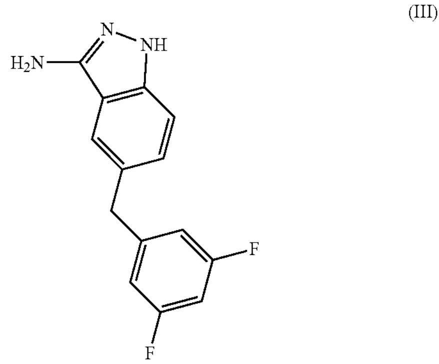 [SMILES: Nc1n[nH]c2ccc(Cc3cc(F)cc(F)c3)cc12]

blocking the addition when the indazol-3-ylamine of formula (III) is completely reacted;

b) deprotecting under mild basic conditions the resulting compound of formula (IV):

(IV)

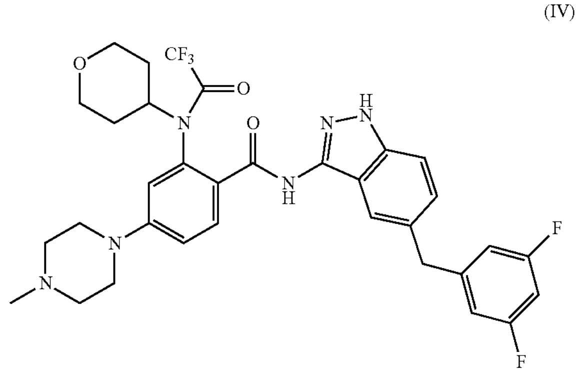 [SMILES: CN1CCN(c2ccc(C(=O)Nc3n[nH]c4ccc(Cc5cc(F)cc(F)c5)cc34)c(N(C(=O)C(F)(F)F)C3CCOCC3)c2)CC1]

to obtain the compound of formula (I) as defined above;

c) suspending in ethanol the obtained compound of formula (I);

d) heating the suspension of step c) to a temperature between about 50° C. and about 70° C. and cooling to room temperature; and e) adding water, filtering and drying to give the crystalline form 4 of compound of formula (I), as defined above.

Preferably, the suspension obtained in step c) is heated to a temperature of about 60° C.

The present invention also discloses a method of preparation of the crystalline Form 4 defined above by conversion of Form 2 into Form 4, which is facilitated by adding an amount of crystalline Form 4 seeds to Form 2.

Accordingly, provided herein is a process for preparing the crystalline Form 4 of N-[5-(3,5-difluoro-benzyl)-1H-indazol-3-yl]-4-(4-methyl-piperazin-1-yl)-2-(tetrahydro-pyran-4-ylamino)-benzamide, which comprises:

f) heating at reflux temperature (about 78° C.) a slurry of crystalline Form 2 of compound of formula (I) as defined above in ethanol and cooling the mixture to a temperature between about 50° C. and about 65° C.;

g) adding an amount of crystalline Form 4 seeds, obtained as defined in steps a) to e), to the mixture of step f), followed by adding water;

h) heating the mixture of step g) at reflux temperature for a time period ranging from 30 to 90 minutes, followed by cooling the mixture to room temperature and stirring for about 12 hours; and i) filtering the mixture of step h) and drying at about 40° C. to obtain the crystalline Form 4 of the compound of formula (I) as defined above.

Preferably, it is provided a process as defined above wherein the solution of step f) is cooled at temperature between 55° C. and 60° C.

In another aspect, it is provided a process as defined above, wherein the mixture of step g) is heated at reflux temperature for about 60 minutes.

Preferably, the amount of Form 4 seeds added to crystalline Form 2 is between 0.05 and 0.5 weight percent of crystalline Form 2. More preferably, the amount of Form 4 seeds added to crystalline Form 2 is about 0.2 weight percent of crystalline Form 2.

In another aspect, provided is a crystalline Form 4, as defined above, prepared by any of the foregoing methods.

The preparation of the compound of formula (I) in crystalline Form 2 is described in the above cited patent application WO20131174876.

The crystalline Form 4 as defined above, can be subsequently formulated with a pharmaceutically acceptable carrier or diluent to provide a pharmaceutical composition.

According to steps a) and b) the reaction conditions are the same as described in WO20131174876 on page 4, lines 15-28.

According to step c) the amorphous compound of formula (I), obtained in step b), is suspended in ethanol.

According to step d), the suspension thus obtained is heated to a temperature between about 50° C. and about 70° C., preferably to about 60° C., until a solution is obtained and then it is cooled to room temperature.

According to step e), to the suspension obtained from step d) is added water and then the resultant precipitate is filtered and dried under vacuum to get crystalline Form 4 of compound of formula (I).

According to step f), a slurry of the crystalline Form 2 of compound of formula (I), obtained as described in the previously cited patent application WO2013/174876 (on page 4, step c2) in ethanol is heated at reflux temperature until a solution is obtained and then cooled to a temperature between about 50° C. and about 65° C., preferably between 55° C. and 60° C.

According to step g), the suspension of step f) is seeded with the crystalline Form 4, then water is added (dripped within at least 15 minutes) to obtain complete precipitation.

According to step h), the mixture of step g) is heated at reflux temperature for a time period ranging from 30 to 90 minutes, preferably for about 60 minutes, and slowly cooled to room temperature. Afterwards, the mixture is stirred for at least 12 hours.

According to step i), the product obtained in step h) is filtered and dried under vacuum at about 40° C. to give the compound of formula (I) in crystalline Form 4.

It is understood that methods detailed herein may be carried out on a production or on a non-production scale.

The new procedure allows obtaining the crystalline Form 4 of compound of formula (I) with high purity and controlling the solid form. This form is suitable for development of an oral formulation.

Crystalline Form 4 as defined above may be administered by any administration route, for instance by oral, parenteral, topical, rectal and nasal route.

The compositions of the invention may be in a form suitable for oral use. Examples of these forms are: tablets, hard or soft capsules, aqueous or oily suspensions, emulsions, dispersible powders or granules. The compositions of the invention may also be in a form suitable for topical use. Examples of these forms are: creams, ointments, gels, or aqueous or oily solutions or suspensions. The compositions of the invention may also be in a form suitable for administration by inhalation such as, for example, finely divided powder or a liquid aerosol. The compositions of the invention may also be in a form suitable for administration by insufflation such as, for example, finely divided powder. The compositions of the invention may also be in a form suitable for parenteral administration (such as, for example, a sterile aqueous or oily solution for intravenous, subcutaneous, intramuscular) or as a suppository for rectal dosing.

The compositions of the invention may be obtained by conventional procedures using conventional pharmaceutical excipients, well known in the art.

Thus, compositions intended for oral use may contain one or more additives such as, for example, colouring, sweetening, flavouring and preservative agents.

For example, the solid oral forms may contain, together with the active compound, acidulants, diluents, e.g., lactose, dextrose, saccharose, sucrose, mannitol, cellulose, corn starch or potato starch; lubricants, e.g., silica, talc, stearic acid, magnesium or calcium stearate, and/or polyethylene glycols; glidants, e.g. colloidal silicon dioxide; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

In another embodiment is provided crystalline Form 4 as defined above for use as a medicament.

In another embodiment is provided crystalline Form 4, as defined above, either alone or in association with other therapeutic agents or radiotherapy, for use in the treatment of a disease state treatable by inhibition of ALK, ROS1, TrkA, TrkB, TrkC, or a combination thereof.

In another embodiment are provided any of the methods of treatment of a patient having cancer, wherein said cancer contains at least one genetic alteration in at least one target gene selected from the group consisting of ALK, ROS1, NTRK1, NTRK2 and NTRK3.

A further object of the invention is to provide a method for treating cancer in a mammal, including a human being, in need of ALK inhibition and/or in a patient having at least one genetic alteration in at least one target gene selected from the group consisting of ALK, ROS1, NTRK1, NTRK2 and NTRK3, such method comprising administering to said mammal a therapeutically effective amount of crystalline Form 4 as defined above.

A further object of the invention is to provide the use of the crystalline Form 4 as defined above, either alone or in association with other therapeutically agents or radiotherapy, for the manufacture of a medicament for the treatment of a disease state treatable by ALK inhibition and/or in a patient having at least one genetic alteration in at least one target gene selected from the group consisting of ROS1, NTRK1, NTRK2 and NTRK3, selected from the group consisting of cancer and cell proliferative disorders.

As used in the present specification, the following words and phrases are generally intended to have the meanings as set forth below, except to the extent that the context in which they are used indicates otherwise.

In the paragraphs defining the x-ray powder diffraction peaks for the crystalline Form 4 of compound of formula (I), the term "about", used for instance in the expression " . . . at a 2-theta value of about . . . " or " . . . at about the 2-theta values . . . ", indicates that the precise positions of peaks (i.e. the recited 2-theta angle values) should not be considered as being absolute values because, as will be appreciated by those skilled in the art, the precise position of the peaks may vary slightly between one machine and another, from one sample to another, or as a result of slight variations in measurement conditions utilised. Generally, a measurement error of a diffraction angle in an x-ray powder diffractogram is about 2-theta=0.5 deg or less (or, more suitably, about 2-theta=0.2 deg or less) and such degree of a measurement error should be taken into account when considering the x-ray powder diffraction patterns Therefore, where it is stated, for example, that the crystalline Form 4 of compound of formula (I), have an x-ray powder diffraction pattern with at least one specific peak at about 2-theta=17.9 degrees (or any one of the other mentioned angles), then this can be interpreted as being 2-theta=17.9±0.5 degrees, or 2-theta=17.9±0.2 degrees. It should be understood that ±0.5 degrees can also be expressed as "plus or minus 0.5 degrees 2θ".

The use of the term "substantially the same as shown in" when referring to an x-ray powder diffraction pattern means that the 2-theta angle values of the pattern may vary slightly from one machine to another, from one sample to another, or as a result of slight variations in measurement conditions, so the peak positions shown in the figures or quoted in the tables are again not to be as absolute values. In this regard, it is known in the art that an x-ray powder diffraction pattern may be obtained which has one or more measurement errors depending on measurement conditions (such as, for example, equipment and/or sample preparation). In particular, it is generally known that intensities in an x-ray powder diffraction pattern may vary depending on measurement conditions and sample preparation. For example, persons skilled in the art of x-ray powder diffraction will realise that the relative intensity of peaks can be affected by, for example, grains above 30 microns in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also affect the result.

Hence a person skilled in the art will appreciate that the diffraction pattern data presented herein are not to be considered as absolute (for further information see "Fundamentals of Powder Diffraction and Structural Characterization", Pecharsky and Zavalij, Kluwer Academic Publishers, 2003).

The term "disease state treatable" means that the treatment according to the invention provides remission of the disease state or at least the conditions and quality of life of the mammal under treatment are improved.

Examples of such disease states are in particular different cancers that may include specific types of cancer including carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratocanthomas, thyroid follicular cancer and Kaposi's sarcoma.

Examples of such disease states are specific types of cancer such as, but not restricted to, breast cancer, lung cancer, such as non-small cell lung cancer, colorectal cancer, prostate cancer, ovarian cancer, endometrial cancer, gastric cancer, pancreatic cancer, papillary thyroid cancer, clear call renal cell carcinoma, uveal melanoma, multiple myeloma, rhabdomyosarcoma, Ewing's sarcoma, Kaposi's sarcoma, and medulloblastoma.

Other examples of such disease states are ALK+ Anaplastic Large Cell Lymphomas (ALCL) and possibly other indications in which the ALK activity might play a role, like neuroblastoma, rhabdomyosarcoma, glioblastoma, inflammatory myofibroblastic tumor, and some kind of melanomas, breast carcinomas, Ewing's sarcomas, retinoblastomas and non-small cell lung carcinomas (NSCLC).

Yet other examples of such disease states are cell proliferative disorders such as, but not restricted to, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

In some embodiments, the crystalline form disclosed herein is formulated for oral administration using pharmaceutically acceptable carriers well known in the art.

In some embodiments, the therapeutically effective dose of the crystalline Form 4 of compound of formula (I), as defined above, or a pharmaceutically acceptable salt, may vary according to the disease, severity of the disorder and the conditions of the patient to be treated. Therefore the physician, as always, must set the optimal dose for each patient. Anyway, the effective dosage range may be from about 10 mg to about 1 g per dose (calculated as a free base), from 1 to 3 times daily.

In some embodiments, the therapeutically effective dose of the crystalline Form 4 of compound of formula (I) is between about 100 mg and about 2000 mg, or between about 100 mg and about 1750 mg, or between about 100 mg and about 1500 mg, or between about 100 mg and about 1250 mg, or between about 150 mg and 1250 mg, or between about 175 mg and about 1250 mg, or between about 200 mg and about 1250 mg, or between 250 mg and about 1250 mg, or between about 300 mg and about 1250 mg, or between about 350 mg and about 1250 mg, or between about 400 mg and about 1250 mg, or between about 400 mg and about 1000 mg, or between about 450 mg and about 950 mg, or between about 450 mg and about 900 mg, or between about 450 mg and about 850 mg, or between about 500 mg and about 850 mg, or between about 500 mg and about 800 mg, or between about 525 mg and about 800 mg, or between about 525 mg and about 775 mg, or between about 550 mg and about 800 mg, or between about 575 mg and about 800 mg, or between about 575 mg and about 775 mg, or between about 600 mg and 800 mg, or between about 600 mg and 775 mg, or between about 600 mg and 750 mg, or between about 600 mg and about 725 mg, or between about 500 mg and about 725 mg, or about between about 500 mg and about 700 mg.

In some embodiments, the therapeutically effective dose of the crystalline Form 4 of compound of formula (I) is about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, or about 1000 mg. In some embodiments, the therapeutically effective dose of the crystalline Form 4 of compound of formula (I) is about 600 mg, taken orally once per day.

EXPERIMENTAL SECTION

The following examples are included to illustrate embodiments of the disclosure, and are not intended to limit the scope of the disclosure.

The crystalline form described herein may be characterized by various methods known in the art, such as x-ray powder diffraction pattern (XRPD) and differential scanning calorimetry (DSC), including, for example, the methods described in Examples 3 and 4.

In one embodiment of the present invention, the crystalline Form 4 is characterized by an x-ray diffraction diagram that is substantially the same as the diagram shown in FIG. 1, with significant peak intensities at about the 2-theta values (deg) described in Table 1. In samples being free of any additional materials (other crystalline forms, excipients), it should be possible to observe the diffraction peaks at about the 2-theta values (deg) described in Table 2.

TABLE 1

Description of the solid state properties and Figures/Table references of crystalline Forms 4 of the compound of formula (I).

Figure 2:
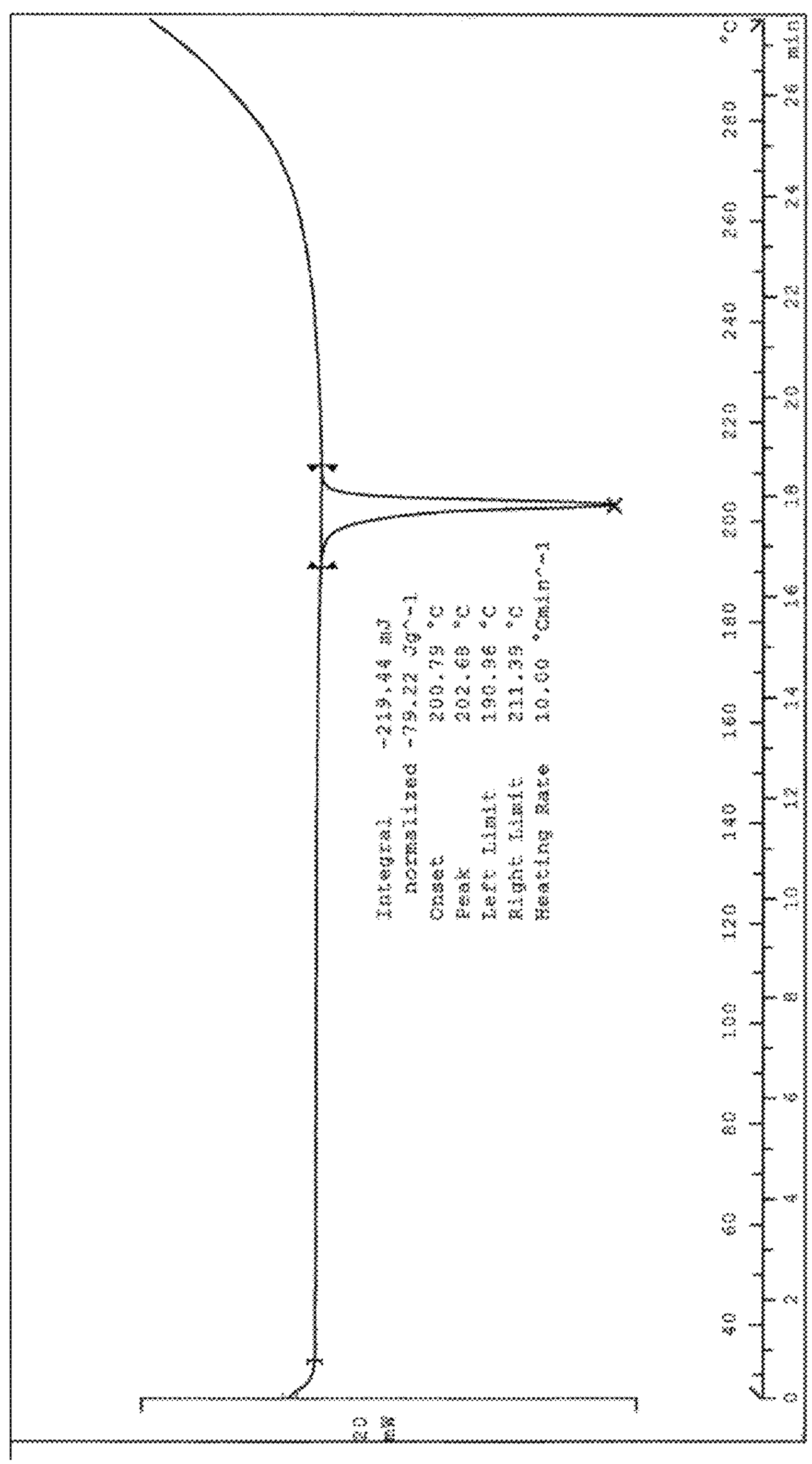
FIG. 2 shows the differential scanning calorimetry (DSC) thermogram of the crystalline Form 4. The thermogram reports temperature (° C.) and time (min) on the x axis, while heat flow (mW) is reported on the y axis.

| Compound (I) | XRPD | DSC | XRPD peaks (2-theta, deg) |
|---|---|---|---|
| Polymorph Form 4 | FIG. 1 Table 2 | FIG. 2 | 8.6, 15.6, 17.9, 19.0, 19.2, 19.6, 19.7, 20.7, 21.3, 22.1, 22.7, 24.3, 24.6 |

In the following Examples, the temperatures are measured in degrees Celsius (° C.) and, unless otherwise indicated, the reactions or experiments take place at room temperature (RT).

Example 1: Preparation of Crystalline Form 4 of Compound of Formula (I)

Steps a) and b) are Described in the Application WO2013174876 on Page 4, Lines 15-28.

Step c)

2.88 Kg of the dried amorphous N-[5-(3,5-difluorobenzyl)-1H-indazol-3-yl]-4-(4-methyl-piperazin-1-yl-2-(tetrahydro-pyran-4-ylamino)-benzamide (compound of formula (I)), obtained by the procedure described in WO20131174876 (steps a and b on pages 3-4), are suspended in about 10 volumes of ethanol (suspension A).

Step d)

20 mL of the suspension A obtained in Step c) are heated to about 60° C. to get a solution, then the solution is cooled to room temperature.

Step e)

20 mL of water are added to the suspension obtained from Step d), and the precipitate is filtered. The product is dried under vacuum to give N-[5-(3,5-difluorobenzyl)-1H-indazol-3-yl]-4-(4-methyl-piperazin-1-yl)-2-(tetrahydro-pyran-4-ylamino)-benzamide as crystalline Form 4 (DSC analysis is reported in FIG. 2).

Example 2: Preparation of the Crystalline Form 4 by Seeding

Step f)

110 mL of ethanol are added to 11.3 g of crystalline Form 2 of 2N-[5-(3,5-difluorobenzyl)-1H-indazol-3-yl]-4-(4-methyl-piperazin-1-yl)-2-(tetrahydro-pyran-4-ylamino)-benzamide, obtained as described in WO2013/174876 (step c2, page 4 and 11-12), and the mixture is heated at reflux until a solution is obtained. The mixture is then cooled to about 58° C.

Step g)

20 mg of seeds of the crystalline Form 4 prepared as described in the Example 1 are added to the mixture of step f); 220 mL of water are then dripped into the mixture within about 15 min obtaining complete precipitation.

Step h)

The mixture thus obtained is heated again to reflux for about 60 min and slowly cooled to room temperature; then it is stirred at room temperature for 12 hours.

Step i)

The precipitate is filtered and dried under vacuum at about 40° C. yielding 9.5 g of crystalline Form 4 of N-[5-(3,5-difluorobenzyl)-1H-indazol-3-yl]-4-(4-methyl-piperazin-1-yl)-2-(tetrahydro-pyran-4-ylamino)-benzamide.

Example 3: Analytical Results by Means of X-Ray Powder Diffraction (XRPD)

The crystalline Form 4 of compound (I) was characterized by x-ray power diffraction (XRPD) performed using a Thermo/ARL XTRA apparatus, irradiating powder samples with a CuKα source (45 kV, 40 mA, 1.8 kW-Kα1 radiation, wavelength λ=1.54060 Angstrom) between 2° and 40° 2-theta at room temperature.

The scan rate was of 1.20°/min (0.020° step with count time of 1 seconds per step).

In the x-ray diffractograms, the angles of diffraction 2-theta are plotted on the horizontal axis (x-axis) and the line intensity on the vertical (y-axis).

As reported in the preceding paragraphs, the crystalline Form 4 of compound of formula (I) provides x-ray powder diffraction patterns substantially the same as the x-ray powder diffraction pattern shown in FIG. 1 and has substantially the most prominent peaks at the 2-theta angle values shown in Tables 1 and 2.

Therefore, it shall be understood that the crystalline Form 4 of compound of formula (I) described in the present invention is not limited to the crystal that provide x-ray powder diffraction pattern identical to the x-ray powder diffraction pattern shown in FIG. 1 and any sample or batch of crystalline Form 4 of compound of formula (I) providing x-ray powder diffraction pattern substantially the same as that shown in FIG. 1 here below falls within the scope of the present invention. A person skilled in the art of x-ray powder diffraction is able to judge the substantial identity of x-ray powder diffraction patterns.

The x-ray diffraction peak positions of crystalline Form 4 is reported in the following Table 2.

TABLE 2

| Crystalline Form 4 of the compound of formula (I) | | |
|---|---|---|
| Position (Deg.) | Intensity (CPS) | Relative Intensity (%) |
| 8.6 | 202.8 | 5.4 |
| 10.3 | 102.0 | 2.7 |
| 11.0 | 206.5 | 5.5 |
| 11.9 | 26.6 | 0.7 |

TABLE 2-continued

| Crystalline Form 4 of the compound of formula (I) | | |
|---|---|---|
| Position (Deg.) | Intensity (CPS) | Relative Intensity (%) |
| 14.3 | 146.3 | 3.9 |
| 14.6 | 68.4 | 1.8 |
| 15.1 | 78.9 | 2.1 |
| 15.3 | 233.9 | 6.3 |
| 15.6 | 992.9 | 26.6 |
| 16.1 | 88.8 | 2.4 |
| 17.1 | 253.2 | 6.8 |
| 17.9 | 3739.3 | 100.0 |
| 19.0 | 478.0 | 12.8 |
| 19.2 | 598.8 | 16.0 |
| 19.6 | 795.1 | 21.3 |
| 19.7 | 711.3 | 19.0 |
| 20.1 | 260.3 | 7.0 |
| 20.7 | 723.7 | 19.4 |
| 21.3 | 1304.4 | 34.9 |
| 22.1 | 459.8 | 12.3 |
| 22.7 | 502.1 | 13.4 |
| 24.3 | 525.6 | 14.1 |
| 24.6 | 420.4 | 11.2 |
| 25.3 | 54.0 | 1.4 |
| 25.5 | 122.3 | 3.3 |
| 25.9 | 255.9 | 6.8 |
| 26.7 | 316.6 | 8.5 |
| 26.9 | 41.5 | 1.1 |
| 27.3 | 107.4 | 2.9 |
| 27.7 | 111.2 | 3.0 |
| 28.1 | 107.3 | 2.9 |
| 28.6 | 116.8 | 3.1 |
| 29.0 | 55.3 | 1.5 |
| 29.5 | 22.7 | 0.6 |
| 29.9 | 56.0 | 1.5 |
| 30.5 | 65.7 | 1.8 |
| 31.0 | 153.5 | 4.1 |
| 31.6 | 42.4 | 1.1 |
| 32.2 | 176.8 | 4.7 |
| 33.3 | 150.8 | 4.0 |
| 34.0 | 73.5 | 2.0 |
| 35.4 | 56.1 | 1.5 |
| 36.4 | 70.4 | 1.9 |
| 36.8 | 39.4 | 1.1 |
| 39.0 | 42.0 | 1.1 |

Example 4: Analytical Results by Means of Differential Scanning Calorimetry (DSC)

DSC analyses were carried out with a Mettler Toledo Star system apparatus. Aluminum DSC pans were loaded with 2-4 mg of sample. The temperature range of the analyses was between 25° C. and a maximum value of 300° C. The samples were analyzed under nitrogen static condition at a heating rate of 10° C./min.

FIG. 2 reports DSC thermograms of the crystalline Form 4.

The observed melting endotherm for crystalline Form 4 is at approximately in the range 200° C.-205° C. (peak temperature) with Delta H in the range 70-82 J/g. It will be understood that the onset and/or peak temperature values of the DSC may vary slightly from one apparatus to another, one method to another or from one sample to another, and so the values quoted are not to be considered as absolute. In fact, observed temperatures will depend on the rate of temperature change as well as sample preparation technique and the particular instrument employed. It will be estimated and taken into account that the temperature values obtained applying such different conditions may vary by plus or minus about 4° C.

The invention claimed is:

1. A method of treating cancer in a mammal comprising: administering to said mammal a therapeutically effective amount of crystalline Form 4 of N-[5-(3,5-difluoro-benzyl)-1H-indazol-3-yl]-4-(4-methyl-piperazin-1-yl)-2-(tetrahydro-pyran-4-ylamino)-benzamide of the following formula (I)

(I)

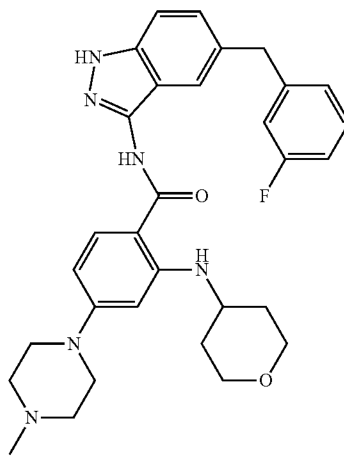

wherein said crystalline form is characterized by an X-ray powder diffraction pattern comprising peaks at 2-theta values of about 8.6, 15.6, 17.9, and 21.3±0.2 degrees, wherein the cancer is selected from the group consisting of a sarcoma, lung cancer, salivary gland cancer, breast cancer, thyroid cancer, pancreatic cancer, ovarian cancer, endometrial cancer, cholangiocarcinoma, and neuroblastoma.

2. The method of claim 1, wherein the mammal is a human being.

3. The method of claim 1, wherein said X-ray powder diffraction pattern further comprises the peaks at 2-theta values of about 19.7, 22.1, and 24.3±0.2 degrees.

4. The method of claim 1, wherein said crystalline form is further characterized by exhibiting a peak in a differential scanning calorimetry scan of from about 200° C. to about 205° C.

5. The method of claim 1, wherein said crystalline form is further characterized by a Delta H in the range 70-82 J/g.

6. The method of claim 1, wherein said X-ray powder diffraction pattern further comprises the peaks at 2-theta values of about 19.6 and 22.7±0.2 degrees.

7. The method of claim 6, wherein said X-ray powder diffraction pattern further comprises the peaks at a reflection angle 2-theta of about 10.3, 11.0, 11.9, 14.3, 14.6, 15.1, 15.3, 16.1, 17.1, 19.0, 19.2, 20.1, 20.7, 24.6, 25.3, 25.5, 25.9, 26.7, 26.9, 27.3, 27.7, 28.1, 28.6, 29.0, 29.5, 29.9, 30.5, 31.0, 31.6, 32.2, 33.3, 34.0, 35.4, 36.4, 36.8, and 39.0±0.2 degrees.

8. A method of treating cancer in a mammal having at least one genetic alteration in at least one target gene selected from the group consisting of ROS1, NTRK1, NTRK2 and NTRK3, comprising: administering to said mammal a therapeutically effective amount of crystalline Form 4 of N-[5-(3,5-difluoro-benzyl)-1H-indazol-3-yl]-4-(4-methyl-piperazin-1-yl)-2-(tetrahydro-pyran-4-ylamino)-benzamide of the following formula (I)

(I)

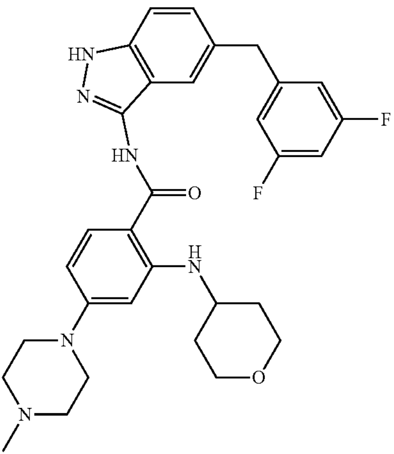

wherein said crystalline form is characterized by an X-ray powder diffraction pattern comprising peaks at 2-theta values of about 8.6, 15.6, 17.9, and 21.3±0.2 degrees.

9. The method of claim 8, wherein the mammal is a human being.

10. The method of claim 8, wherein said X-ray powder diffraction pattern further comprises the peaks at 2-theta values of about 19.7, 22.1, and 24.3±0.2 degrees.

11. The method of claim 8, wherein said crystalline form is further characterized by exhibiting a peak in a differential scanning calorimetry scan of from about 200° C. to about 205° C.

12. The method of claim 8, wherein said crystalline form is further characterized by a Delta H in the range 70-82 J/g.

13. The method of claim 8, wherein said X-ray powder diffraction pattern further comprises the peaks at 2-theta values of about 19.6 and 22.7±0.2 degrees.

14. The method of claim 13, wherein said X-ray powder diffraction pattern further comprises the peaks at a reflection angle 2-theta of about 10.3, 11.0, 11.9, 14.3, 14.6, 15.1, 15.3, 16.1, 17.1, 19.0, 19.2, 20.1, 20.7, 24.6, 25.3, 25.5, 25.9, 26.7, 26.9, 27.3, 27.7, 28.1, 28.6, 29.0, 29.5, 29.9, 30.5, 31.0, 31.6, 32.2, 33.3, 34.0, 35.4, 36.4, 36.8, and 39.0±0.2 degrees.

15. The method of claim 1, wherein the cancer is selected from the group consisting of a sarcoma, lung cancer, salivary gland cancer, breast cancer, thyroid cancer, and pancreatic cancer.

16. The method of claim 1, wherein the cancer is selected from the group consisting of non-small cell lung cancer, a sarcoma, mammary analog secretory carcinoma (MASC), breast cancer, and thyroid cancer.

17. The method of claim 1, wherein the cancer is selected from the group consisting of non-small cell lung cancer, a sarcoma, and mammary analog secretory carcinoma (MASC).

18. The method of claim 8, wherein said cancer is a non-small cell lung cancer and said at least one target gene is ROS1.

19. The method of claim 8, wherein said cancer is a solid tumor and said at least one target gene is selected from at least one of NTRK1, NTRK2, and NTRK3.

20. The method of claim 8, wherein said cancer is selected from non-small cell lung cancer, papillary thyroid cancer, neuroblastoma, pancreatic cancer and colorectal cancer.

21. The method of claim 20, wherein said cancer is selected from non-small cell lung cancer, neuroblastoma, and colorectal cancer.

22. The method of claim 8, wherein the cancer is selected from the group consisting of a sarcoma, lung cancer, salivary gland cancer, breast cancer, thyroid cancer, colorectal cancer, and pancreatic cancer.

23. The method of claim 8, wherein the cancer is selected from the group consisting of non-small cell lung cancer, a sarcoma, mammary analog secretory carcinoma (MASC), breast cancer, and thyroid cancer.

24. The method of claim 8, wherein the cancer is selected from the group consisting of non-small cell lung cancer, a sarcoma, and mammary analog secretory carcinoma (MASC).

* * * * *